United States Patent
Foley et al.

[19]

[11] Patent Number: 5,817,077
[45] Date of Patent: Oct. 6, 1998

[54] VAGINAL MOISURE BALANCE TAMPON AND PROCESS

[75] Inventors: Theodore A. Foley, East Brunswick; Linda M. Pierson, Hillsborough; Harry L. Pine, North Brunswick; Ronald P. Schreck, Tinton Falls, all of N.J.

[73] Assignee: McNeil-PPC, Inc., Skillman, N.J.

[21] Appl. No.: 814,688

[22] Filed: Mar. 11, 1997

Related U.S. Application Data

[60] Continuation of Ser. No. 427,790, Apr. 25, 1995, abandoned, which is a division of Ser. No. 251,543, May 31, 1994, abandoned.

[51] Int. Cl.$^6$ .................................................. A61F 13/15
[52] U.S. Cl. ........................ 604/363; 604/904; 604/378
[58] Field of Search ................................ 604/1–3, 365, 604/378, 904, 363

[56] References Cited

U.S. PATENT DOCUMENTS

| | | |
|---|---|---|
| 2,330,257 | 9/1943 | Bailey . |
| 2,710,007 | 6/1955 | Greiner et al. . |
| 2,761,449 | 9/1956 | Bletzinger . |
| 3,055,369 | 9/1962 | Graham, Jr. . |
| 3,322,123 | 5/1967 | Griswold et al. . |
| 3,340,874 | 9/1967 | Burgeni . |
| 3,683,912 | 8/1972 | Olson et al. . |
| 3,815,601 | 6/1974 | Schaefer . |
| 3,838,692 | 10/1974 | Levesque . |
| 3,929,135 | 12/1975 | Thompson . |
| 3,967,623 | 7/1976 | Butterworth et al. . |
| 3,976,075 | 8/1976 | Chinai et al. . |
| 3,994,298 | 11/1976 | Des Marais . |
| 4,020,841 | 5/1977 | Poncy et al. . |
| 4,056,103 | 11/1977 | Kaczmarzyk et al. . |
| 4,239,043 | 12/1980 | Gellert . |
| 4,305,391 | 12/1981 | Jackson . |
| 4,341,214 | 7/1982 | Fries et al. . |
| 4,475,911 | 10/1984 | Gellert . |
| 4,486,191 | 12/1984 | Jacob . |
| 4,710,185 | 12/1987 | Sneyd, Jr. et al. . |
| 4,735,843 | 4/1988 | Noda . |
| 4,743,237 | 5/1988 | Sweere . |
| 4,816,100 | 3/1989 | Friese . |
| 4,859,273 | 8/1989 | Friese . |
| 4,863,450 | 9/1989 | Friese . |
| 4,929,480 | 5/1990 | Midkiff et al. . |
| 5,004,467 | 4/1991 | Hinzmann et al. . |
| 5,006,116 | 4/1991 | Alikhan et al. ..................... 604/904 |
| 5,185,010 | 2/1993 | Brown, Jr. . |
| 5,350,371 | 9/1994 | Van Iten ............................... 604/904 |
| 5,364,383 | 11/1994 | Hayes et al. . |
| 5,374,258 | 12/1994 | Lloyd et al. ......................... 604/904 |

FOREIGN PATENT DOCUMENTS 2043434  12/1991  Canada .

OTHER PUBLICATIONS

K. Shands et al. "Toxic Shock Syndrome: The Emerging Picture", Annals of Internal Medicine, vol. 94, No. 2, Feb. 1981.

T. Sveda, Jr. et al. "Foam/Fabric Interaction Under Shear", Textile Research Journal, Nov. 1986, pp. 674–678.

G. Wagner et al. "Tampon–induced changes in vaginal oxygen and carbon dioxide tensions" Am. J. Obstet. Gynecol. Jan. 15, 1984, pp. 147–150.

(List continued on next page.)

*Primary Examiner*—Robert A. Clarke
*Assistant Examiner*—Dennis Ruhl

[57] ABSTRACT

Vaginal epithelium drying is substantially reduced or prevented by reducing the capillary suction pressure of a tampon in early use. This is accomplished by modifying the capillary suction pressure of the surface of the tampon by using hydrophobic components in the tampon, such as hydrophobic fibers and/or hydrophobic cover material. Other means of obtaining a lower capillary suction pressure include increasing the denier of the fibers in the tampon's absorbent core and/or decreasing the density of the tampon.

8 Claims, 2 Drawing Sheets

OTHER PUBLICATIONS

G. Wagner et al. "Vaginal Physiology During Menstruation", Annals of Internal Medicine, 1982, vol. 96 (Part 2) pp. 921–923.

S. Weissberg, MD, et al. "Recurrent Vaginal and Cervical Ulcers Associated with Tampon Use", JAMA, Sep. 16, 1983, vol. 250, No. 11, pp. 1430–1431.

"Toxic Shock Syndrome Assessment of Current Infor. And Future Research Needs", Report of a Study Institute of Medicine, Div. Of Health Sci. Policy, Div. Of Health Promotion and Disease Prevention.

Steven D. Jimerson, Jr. et al. "Vaginal Ulcers Associated with Tampon Usage", Obstetrics & Gynecology, vol. 56, No. 1, Jul. 1980, pp. 97–99.

Stephen M. Larkin, MD et al., "Toxic Shock Syndrome: Clinical, Laboratory, and Pathologic Findings in Nine Fatal Cases", Annals of Internal Med. 1982, vol. 96, (Part 2) pp. 858–864.

R. Levin et al. "Absorption of menstrual discharge by tampons inserted during mensturation: quantitative assessment of blood and total fluid content" B. Journ. of Obstet. & Gynec. Jul. '86, vol. 93, pp. 765–772.

B. Miller et al. An extended Range Liquid Extrusion Method for Determining Pore Size Distributions, Textile Research Journal, Jan. 1986, pp. 35–40.

A. Onderdonk, et al. "Quantitative Assessment of Vaginal Microflora during Use of Tampons of Various Compositions", Appl. Environ. Microbiol. Dec. 1987, pp. 2774–2778.

D. Raudrant et al. Study of the vaginal mucous membrane following tampon utilisation; . . . E. Journ. of Obstetrics & Gynecology & Repro. Biol. vol. 31, 1989, pp. 53–65.

M. Raum, et al. "Toxic Shock Syndrome with Vaginal Ulceration", J. Fla. M.A. Oct. 1980, vol. 67, No. 10, pp. 935–936.

Kathryn F. Barrett, B.S. et al. "Tampon–induced vaginal or cervical ulceration" Am. J. Obstet. Gynecol. Feb. 1, 1977, vol. 127, No. 3, pp. 332–333.

Alan S. Berkeley MD et al. "The Potential of Digitally Inserted Tampons to Induce Vaginal Lesions", Obstetrics & Gynecology, vol. 66, No. 1, Jul. 1985, pp. 31–35.

John D. Blair M.D. et al. "Tampon–Related Toxic–Shock Syndrome", A.J.C.P. Sep. '82 vol. 78, No. 3, pp. 372–376.

A.A. Burgeni et al. Capillary Sorption Equilibria in Fiber Masses, Textile Research Journal, vol. 37, No. 5, May 1967, pp. 356–366.

William E. Crowder, Jr. MD et al. "Colposcopic Diagnosis of Vaginal Ulcerations in Toxic Shock Syndrome" Obstetrics & Gynecology, vol. 61, No. 3 (Suppl.), Mar. 1983 pp. 505–535.

H. Fox, "The pathology of tampon usage and of the toxic shock syndrome", Postgraduate Med. Journal, 1985, 61 (Suppl. 1), pp. 31–33.

I.S. Fraser et al. "Blood and Total Fluid Content of Menstrual Discharge", Obstetrics & Gynecology, vol. 65, No. 2, Feb. 1985, pp. 194–198.

Eduard G. Friedrich, Jr. MD "Tampon Effects on Vaginal Health", Clinical Obstetrics & Gynecology, vol. 24, No. 2, Jun. 1981 pp. 395–406.

Eduard G. Friedrich, Jr. MD et al. "Tampon–Associated Vaginal Ulcerations", Obstetrics & Gynecology, vol. 55, No. 2, Feb. 1980, pp. 149–156.

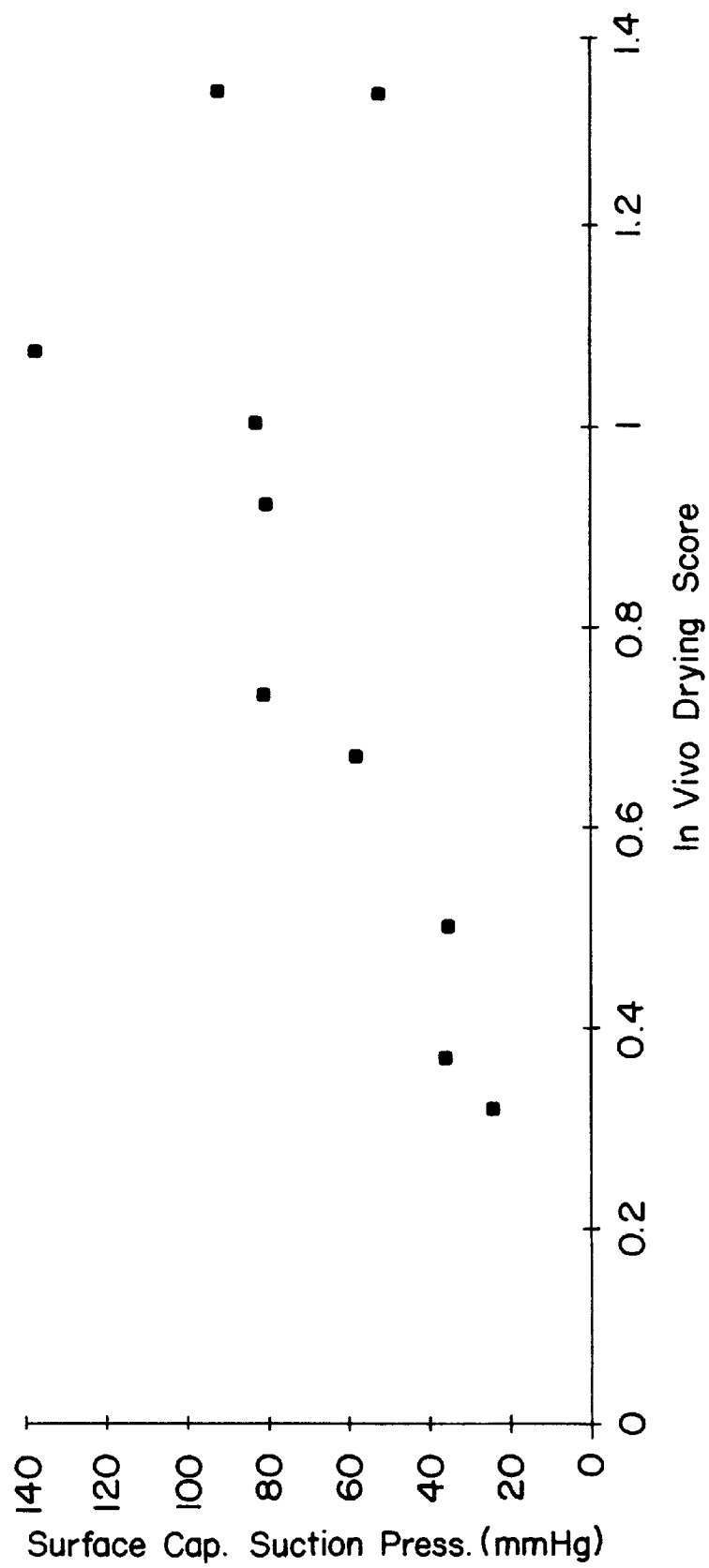

VAGINAL MOISTURE BALANCE TAMPON AND PROCESS

This is a continuation of application Ser. No. 08/427,790, filed Apr. 25, 1995 now abandoned, which was a divisional application of Ser. No. 08/251,543, filed May 31, 1994, now abandoned, which is incorporated herein by reference.

This invention relates to personal care products and particularly to tampons having high fluid absorbent capacity and yet do not cause the vaginal epithelial tissue to dry. This invention also relates to methods of constructing such tampons.

Those familiar with the art of making and using internal vaginal tampons have long been aware that the use of these tampons can cause drying of vaginal epithelial tissue. Drying may cause many irritating vaginal conditions and may lead to discomfort and infection, affecting the health of the tampon wearer.

DESCRIPTION OF THE PRIOR ART

Although women appreciate that the use of vaginal tampons during menstruation is convenient and discreet, they have found many disadvantages and inconveniences attendant upon tampon use. For example, tampons may unexpectedly leak if they do not expand fully to fill the vaginal canal. The tampons may also become saturated with menstrual fluid unbeknownst to the wearer and begin to leak. Tampons are sometimes hard to insert into or remove from the vaginal canal. The tampons' absorbent cores sometimes slough off, leaving absorbent fibers in the vagina.

There have been many attempts to remedy these problems by manipulating elements of the tampon's absorbent core and overwrap.

U.S. Pat. No. 2,710,007, (Greiner, et al.) and U.S. Pat. No. 3,340,874 (Burgeni) are examples of the use of low density material in portions of a tampon plug in order to promote rapid absorption of fluid.

Some references describe the use of one or two hydrophobic covers to protect the inner core fibers from sloughing and/or to improve the tampon's lubricity on insertion and withdrawal without reducing the speed of fluid uptake. For example, U.S. Pat. No. 3,055,369 (Graham) and U.S. Pat. No. 3,683,912 (Olson, et al.) describe tampons having an overwrap or sheath of nylon, Orlon, Saran, Dacron or polypropylene.

U.S. Pat. No. 3,815,601 (Schaefer) describes a tampon containing a body of pieces of foam encased in a fine mesh tubular overwrap made of a nonwoven fabric of cotton-rayon or polyester. The overwrap is doubled over on itself. The hydrophobic overwrap is intended to insulate the vaginal wall from collected menses.

U.S. Pat. No. 3,994,298, to Des Marais, describes a tampon with improved wet expansion characteristics, composed of a lubricated foam material treated with a nonionic surfactant. The foam is contained in a fluid permeable overwrap such as that described in Schaefer.

U.S. Pat. No. 3,976,075, (Chinai, et al.) describes an absorbent pad covered, at least on one surface, with a non-occlusive pattern (5% to 75% of the surface area) of an adhesive binder, which serves to prevent sloughing and telescoping of the absorbent pad without decreasing absorptivity.

U.S. Pat. No. 4,239,043 (Gellert) describes a tampon made of blocks of hydrophilic polyester foam or foam-fiber composites in an elongated closed-end fluid permeable sheet material of hydrophilic, hydrophobic or partially hydrophobic polymer such as polyester.

U.S. Pat. No. 4,305,391 (Jackson) describes a tampon composed of a superabsorbent-containing core and two fluid permeable, hydrophobic wraps that aid withdrawal of the tampon and prevent reverse flow from a saturated tampon.

U.S. Pat. No. 4,341,214 (Friese et al.) describes a tampon of a cylinder of hydrophobic foam in a fluid-permeable woven or nonwoven sleeve.

Other patents discuss the shielding of the absorbent tampon core by an occlusive cover. For example, U.S. Pat. Nos. 2,330,257 (Bailey); 4,020,841 (Poncy et al.); and 4,816,100, 4,859,273 and 4,863,450 (Friese) relate to such tampons.

There are several examples in the prior art in which a hydrophilic cover is used as a protective and lubricating interface between the vagina and the highly absorbent core of a tampon. Such a cover is also used to reduce excessive sloughing of fibers from the tampon core to the vaginal wall. Examples of such references are U.S. Pat. Nos. 3,322,123 (Griswold et al.), 4,056,103 (Kaczmarzyk et al.) and 5,006,110 (Alikhan et al.).

Other prior art patents describe blending fibers in the core of the tampon including synthetic, resilient fibers, for improved force and speed of expansion. Examples of such patents are U.S. Pat. Nos. 2,761,449 (Bletzinger) and 4,475,911 (Gellert).

Although many of the tampon structures described above are directed to increasing absorbency and rate of absorbency, not one is concerned with the effect of such increased absorbency on the walls of the vagina. Medical literature reports strong links between standard catamenial tampons and drying lesions in the vaginal epithelium. The reported degree of drying ranges from mild, to moderate causing a wrinkling of the vaginal mucosa, to severe causing layering and peeling, to microulceration, and finally, to frank, gross ulceration. The frequency of occurrence of each level of damage decreases with increasing severity of the damage. One example of this type of study is Raudrant et al., "Study of the Vaginal Mucous Membrane following Tampon Utilization: Aspect on Colposcopy, Scanning Electron Microscopy and Transmission Electron Microscopy", *European J. of O.B. Gyn. & Reprod. Biology*, Vol. 31, pp. 53–61 (1989), which reports that high-absorbency tampons can cause drying of the vaginal epithelium, which in turn, may result in abrasions.

It is, therefore, an object of this invention to provide novel tampon products that have a high degree of absorbency, yet do not cause excessive drying of the vaginal epithelium.

SUMMARY OF THE INVENTION

The products of this invention aid in preventing drying of the vaginal wall which may come about as a result of tampon use. They accomplish this by substantially minimizing the tampons' potential to wick moisture from the vaginal wall to the tampon while allowing the tampon's absorbent core to absorb menstrual or other vaginal secretions. By preventing drying, normal vaginal moisture conditions during tampon wear are maintained.

Clinical studies have shown that vaginal epithelial drying is caused in part by the rapid initial uptake of its natural moisture, as well as the secretions of the vagina and uterus, when a dry, unused tampon is placed in close proximity to the vaginal epithelium. Uptake of vaginal epithelium moisture occurs because of the tendency of the substrates in the system, i.e., the moist vaginal epithelium and the dry, highly absorbent tampon, to equilibrate their relative moisture content. This loss of moisture is due to capillary suction pressure of the absorbent surface as well as the core of the tampon. Increased dryness can cause discomfort, because the vaginal wall may resist withdrawal of the tampon without an appropriate amount of fluid and secretions. This resistance results in an increased likelihood of causing epithelial abrasions.

According to this invention, the reduction of vaginal epithelium drying due to tampon use is accomplished by one or more techniques intended to reduce capillary suction pressure-induced wicking of moisture from the vaginal epithelium by the tampon:

First, a particular kind of outer wrap for the tampon may be used to reduce capillary suction pressure by the tampon. For instance, decreasing the tampon's capillary suction pressure may be accomplished by decreasing the hydrophilicity of a substantial thickness of the outer portion of the tampon, i.e., by increasing the contact angle with water of the material forming the outer portion of the tampon.

Second, the composition of the absorbent core of the tampon may be adjusted in order to reduce capillary suction pressure. Reducing vaginal wall drying due to tampon use can also be accomplished by decreasing the capillary suction pressure of the core of the tampon by introducing, in substantial amounts, hydrophobic fibers together with hydrophilic fibers in a blend of fibers in the tampon's absorbent core. The hydrophobic fibers may be made wettable, without reducing their inherent resiliency, by coating them with a surfactant such as polysorbate-20 and the like. Yet another means to reduce the capillary suction pressure of the tampon is to increase the diameter of the fibers in the tampon core to reduce capillary suction pressure or to decrease the density of the tampon core.

The net result of any of these methods is a substantial decrease in the capillary suction pressure of the tampon upon insertion, i.e., when the tampon is unsaturated. One or more of these methods may be used in reducing the drying power of a tampon. Of course, the greater number of methods employed, the lower the risk of drying the vaginal epithelium. For instance, a combination of hydrophobic outer wrap, core fiber blends containing hydrophobic fibers, increased fiber diameter in the core and reduced core density can result in a highly effective tampon having substantially reduced epithelial tissue drying power.

BRIEF DESCRIPTION OF THE DRAWING

FIG. 2 is a graph illustrating the relationship between capillary suction pressure and in vivo drying scores for several commercial tampons and for several embodiments of the present invention.

DETAILED DESCRIPTION OF THE PREFERRED EMBODIMENT

Figure 1:
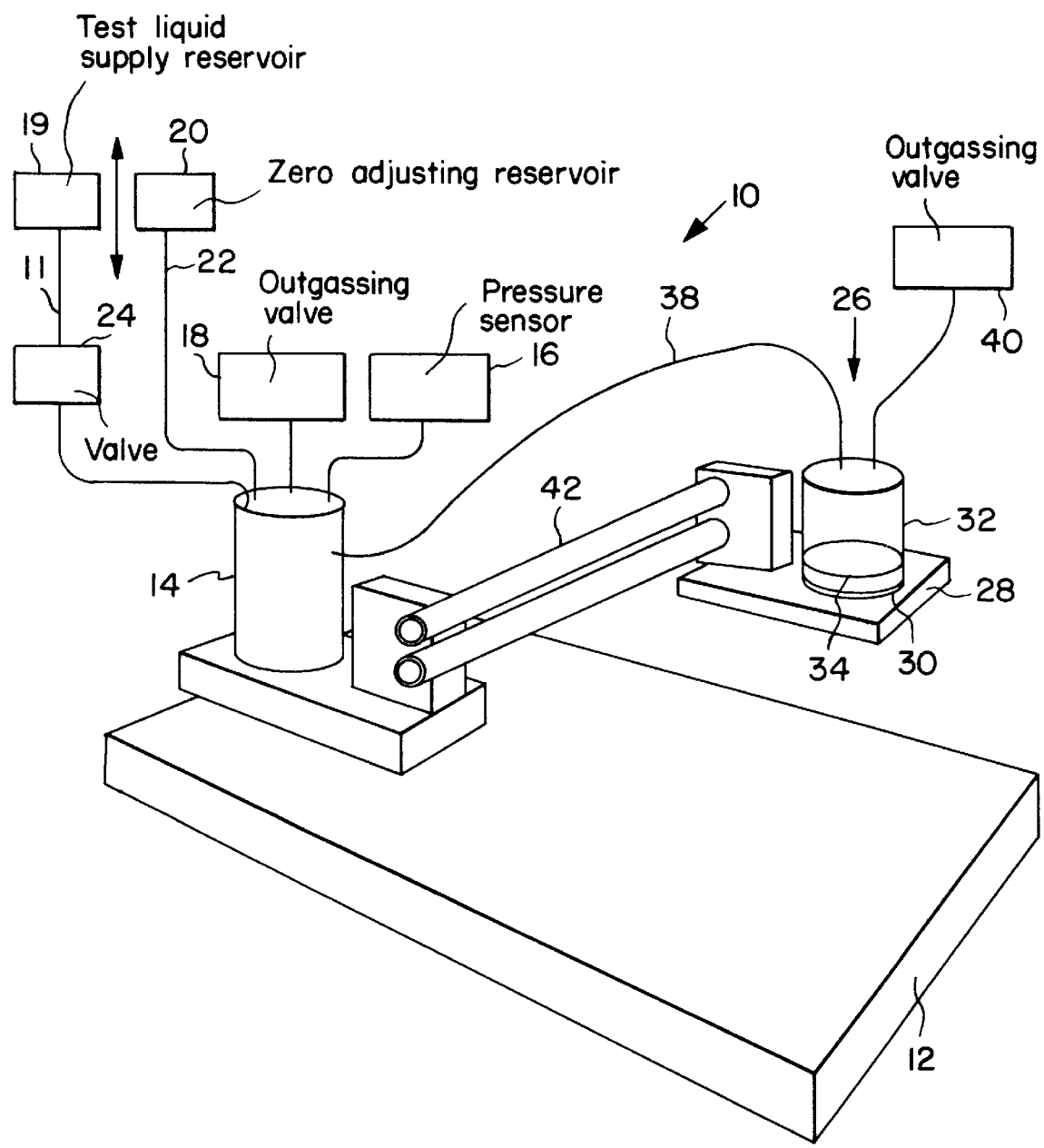
FIG. 1 illustrates a capillary suction pressure testing device.

We have discovered that significant drying of the vaginal epithelium can lead to increased health risks for the tampon user. Increased drying appears to be independent of the type of fiber currently used in tampon manufacture. We have discovered that drying can be significantly reduced by reducing the capillary suction pressure of the tampon or by interrupting the capillary suction pressure of the tampon by positioning a substantially hydrophobic cover membrane between the tampon's absorbent core and the vaginal epithelium during use.

Thus, this invention provides novel tampon products and methods of using such tampon products which prevent drying of the vaginal wall. Prevention of drying is especially important on insertion and during menstrual flow into the unsaturated tampon, when drying is most likely to occur. The tampons of this invention prevent drying while allowing the absorbent core of the tampon to perform in a conventional manner and absorb menstrual flow and/or other secretions.

A tampon cover must be capable of passing body fluids for absorption by the core material. In the products of this invention, the cover permits the passage of fluid under a much lower capillary suction pressure than covers of conventional products. We have found that a capillary suction pressure of less than about 40 mm Hg can substantially reduce vaginal epithelial drying. Preferably the capillary suction pressure is less than about 30 mm Hg, and more preferably, less than about 25 mm Hg. Capillary suction pressure values of current and former commercial tampons are set forth in Table 1, below.

TABLE 1

| Tampon | Surface Capillary Suction Pressure (mm Hg) |
|---|---|
| Tampax Compak ™ Regular | 137 |
| Playtex ™ Plastic Regular | 79.9 |
| .o.b. ™ Regular | 82.3 |
| Playtex Ultimates ™ | 91.7 |
| Kotex Security ™ Regular | 52 |
| Tampax ™ Original Regular | 78.8 |
| Rely ™ Regular | 42.1 |

Strong capillary suction pressure may be reduced in accordance with this invention by covering substantially most or all of the outer surfaces of the tampon that contact the vaginal epithelium, with a relatively hydrophobic, but porous cover. For example, a sleeve or sheath of apertured plastic film may be used to cover the side walls of conventional tubular tampons. Preferably, the cover should also envelope the insertion end of the tampon. Most preferably, the cover should surround the withdrawal end of the tampon as well. Alternatively, a woven or non-woven web of natural or synthetic fibers which has been heat-set or bonded together by adhesives can be used. For example, the sleeve may be a spun-bonded filamentary web of hydrophobic polymers such as polyester or the like. While, in some embodiments of the present invention, a cover having a basis weight of less than about 0.25 oz/yd$^2$, it is preferred that the cover material have a basis weight of at least about 0.25 oz/yd$^2$, more preferably about 0.75 oz/yd$^2$. The thickness of a preferred cover material, a thermally bonded fabric having a basis weight of 0.25 0.25 oz/yd$^2$ which was made of 3 denier bicomponent (polyethylene over PET) fiber (BASF Merge 1050, available from BASF), is about 0.004 to 0.008 inches.

In order to increase the thickness of the cover material, multiple cover layers can be used. Multiple layers have been found to reduce vaginal epithelium drying even when capillary suction pressure is somewhat higher than single-ply covers or tampons with no cover at all. Therefore, two layered covers are useful to reduce vaginal epithelium drying, and preferably four or more layers can be used in the practice of the present invention. In a particularly preferred embodiment, when only increased cover thickness is used to reduce vaginal epithelium drying, as many as eight layers can be used in the cover material.

For the purposes of this invention, a material is considered to be "hydrophobic" if it is not easily wetted by water. Preferably, the hydrophobic material exhibits a contact angle with water of equal to or greater than about 90°. Hydrophobic fibers, hydrophilic fibers treated with water repellant finishes, reticulated films and apertured films are suitable for use as the hydrophobic material in the products of this invention.

An example of a hydrophobic outer wrap or cover is an apertured, non-absorbent cover material such as a reticulated plastic film. This cover creates a discontinuity between the absorbent core and the vaginal epithelium thereby substantially reducing the capillary suction pressure of the absorbent core on the vaginal epithelium.

In another embodiment of the products of this invention, a fibrous outer wrap layer may be a blend of both hydrophilic and hydrophobic natural or synthetic fibers having the appropriate characteristics to provide the decreased vaginal epithelium drying effect of the tampons of the invention. Examples of hydrophilic fibers are cotton, rayon, wood pulp and hydrophobic fibers that have been treated to reduce their contact angle with water. Such treatments include, without limitation, corona treatments, surfactant treatments, chemical etching, plasma treatments, and the like. Examples of hydrophobic fibers are polypropylene, polyesters and polyamides or multicomponent fibers wherein one component such as polyester is enveloped by or is alongside with another component such as polyethylene, polypropylene or a lower-melting polyester.

Alternatively, a moisture resistant, hydrophobic material such as a fluorocarbon may be applied to the tampon surface during its manufacture by spraying, printing, coating, and the like, the hydrophobic material on the surface according to means known to those of skill in the art.

Another means of reducing the capillary suction pressure of the tampon is by reducing the capillary suction pressure of the absorbent core. One means of reducing capillary suction pressure is by reducing the amount of hydrophilic fibers in the core and replacing them with hydrophobic fibers such as polyester and polypropylene. Thus, from about 10 to about 90% of the absorbent core fibers can be hydrophobic. However, it is preferable to have between about 20 and about 80% of the fibers to be hydrophobic and, even more preferably, between about 30 and about 70% of the fibers to be hydrophobic. These compositions will achieve the result of reducing the capillary suction pressure of the tampon while providing sufficient absorbent capacity and retention to absorb and to hold onto menstrual fluid with which it comes into contact.

Another means for reducing capillary suction pressure is by using higher-denier fibers. These higher-denier fibers have larger diameters than low-denier fibers. Preferably, the denier of the fibers which make up the absorbent core should be at least 3. Larger fibers create an absorbent structure with larger interfiber openings and are more resilient. Thus, they create and maintain larger pores or capillaries between fibers. These larger pores provide adequate spaces through which fluid can pass, but their capillary suction pressure is relatively low. Structures with larger pores do not wick as strongly as structures with smaller pores.

In another embodiment of the products of this invention, the density of the absorbent core is low, preferably no greater than about 0.25 g/cc. More preferably, the density should be about 0.2 g/cc or less. However, in embodiments of this invention incorporating several of the drying-reduction techniques, the density of the tampon may be as great as 0.4 g/cc.

Two or more of the techniques set forth above may combined to make a reduced-capillary suction pressure tampon. Most preferably, all the techniques set forth herein are employed for maximum reduction of drying of the vaginal epithelium. Thus, for example, a tampon product according to this invention may have a hydrophobic cover or outer wrap covering the entire tampon and a low-density absorbent core containing both high-denier hydrophobic and hydrophilic fibers in order to achieve a low-capillary suction pressure product.

The tampon of the present invention can be made according to processes known in the art. One particular method is described below in Example 2. Generally, a sliver of hydrophilic fibers is formed and cut to the length necessary to form a single tampon. For example, this may be about 1.4 g of the hydrophilic fibers. The cut sliver may be placed onto a piece of cover material and wrapped to form a covered tampon pledget. A string for use to withdraw a soiled product may be pierced and looped through the tampon blank. This blank may be compressed to form the tampon product.

This invention is further described but not limited by the following examples.

EXAMPLE 1

In vivo Results—Effect of a Non-wicking Cover

A comparison was made of the drying effects of a control product, a regular-absorbency commercial tampon (Tampax Compak™ brand) and one made by encasing a second commercial tampon (o.b.™ tampon, available from McNeil-PPC, Inc.) with a non-permeable polyethylene film. Ten panelists were each given a colposcopic internal exam just prior to insertion of either the test product or control product. The choice of which product each panelist wore was made randomly. The test was conducted while the panelists were not menstruating and lasted three hours. After three hours, the tampons were removed from the panelists. Each panelist then again underwent a colposcopic examination to determine whether she had vaginal drying, layering or ulcerations. Each panelist tested both tampons. The panelists waited a minimum of two days before testing the second tampon.

The results of this test were determined by assigning "drying scores" to each panelist based upon visual examination. Drying scores were based on internal examination were as follows:

0—no drying
1—slight drying
2—moderate drying
3—severe drying with layering
4—severe drying with microulceration The results of the tests and examinations are set forth in Table 2.

TABLE 2

| Score | Tampax Compak ™ | o.b. ™ Tampon Enclosed in a polyethylene film |
|---|---|---|
| 0 | 5 | 10 |
| 1 | 6 | 0 |
| 2 | 2 | 0 |
| 3 | 2 | 0 |
| 4 | 0 | 0 |
| Totals | 15 | 10 |
| Avg. Score | 1.07 | 0 |

Although non-absorbent tampons do not absorb, this test showed that the vaginal moisture balance can be influenced by completely limiting the tampon's absorbing ability, and thereby preventing the occurrence of vaginal drying.

EXAMPLE 2
Effects of Various Hydrophobic Fibrous and Perforated Film Covers

An in vivo test was performed with 15 panelists. The products tested were as follows: Product A, a control, uses a commercial tampon (Tampax Compak™ Regular) with a rayon cotton core and a chemically bonded rayon nonwoven cover. Product B was a tampon made in accordance with the teachings of this invention that contained 100% carded rayon fibers in its absorbent core and was covered circumferentially, but not at either end, by a 0.75 oz/yd$^2$ fluorocarbon-treated, chemically bonded polyester nonwoven material. Product C was another embodiment of the product of this invention, having the same absorbent core as product B and having a Reticulon™ brand perforated polyethylene/ethylene vinyl acetate bilayer film cover having a basis weight of 1.25 oz/yd$^2$ (Reticulon)™ #6003, available from Johnson & Johnson Advanced Materials Company) completely encasing the tampon and covering both ends of the tampon.

In forming Product B, approximately 1.4 g of the carded rayon fibers were wrapped in the cover material to form a blank approximately 2.5" long by 1" diameter. A short length of white rayon string was placed through the blank, and the blank was compressed in a die having a diameter of 0.43". After the tampon was compressed, it was transferred to an applicator for use. All tampons were Regular Absorbency, as measured by the Syngina Test. This test is described in Federal Register, Part III, Department of Health and Human Services, Food and Drug Administration (21 CFR Part 801, pp. 37263-4, Sept. 23, 1988). The protocol and evaluation of panelists was the same as that used in Example 1.

TABLE 3

| Score | Product A Control | Product B Fluorocarbon Tr. Cover | Product C Reticulon ® Cover |
|---|---|---|---|
| 0 | 5 | 8 | 7 |
| 1 | 6 | 4 | 7 |
| 2 | 2 | 2 | 0 |
| 3 | 2 | 1 | 1 |
| 4 | 0 | 0 | 0 |
| Total | 15 | 15 | 15 |
| Avg. Score | 1.07 | 0.73 | 0.67 |

The Control Product A was the same as that of Example 1. These data illustrate that covering the tampon with a hydrophobic fibrous or perforated film cover substantially reduced the vaginal epithelial drying.

EXAMPLE 3
Effects of Multiple Layers of Hydrophobic Cover

A Regular Absorbency tampon having a 100% rayon core, Product D, was completely covered, top, bottom, and sides, with eight layers of a thermally bonded fabric having a basis weight of 0.25 oz/yd$^2$ which was made of 3 denier bicomponent (polyethylene over PET) fiber (BASF Merge 1050, available from BASF), was formed according to the procedure of Example 2, and was compressed. The tampon product was tested for vaginal drying. This embodiment of the product of this invention was intended to separate the absorbent tampon core from the vaginal tissue with a relatively thick, hydrophobic layer. The protocol and evaluation of the panelists was the same as that used in Example 1. The results are shown in Table 4, below.

TABLE 4

| Score | Product A Control | Product D 8 Layer Bicomponent Fiber Cover |
|---|---|---|
| 0 | 5 | 7 |
| 1 | 6 | 4 |
| 2 | 2 | 1 |
| 3 | 2 | 0 |
| 4 | 0 | 0 |
| Totals | 15 | 12 |
| Avg. Score | 1.07 | 0.5 |

The Control Product A was the same as that of Example 1. These data illustrate that covering the tampon with a thick hydrophobic fibrous cover substantially reduces vaginal epithelial drying.

EXAMPLE 4
Effects of Rayon/Polyester Absorbent Blend In The Core

A Regular Absorbency tampon Product E containing a blend of 50% rayon and 50% polyester fibers (SN2325, a 3 denier rayon fiber available from Courtaulds, and 374W, a 5.5 denier polyester fiber available from duPont, respectively) in the core was formed according to the process of Example 2. The tampon was covered on its top, bottom and sides with one layer of the cover material of Example 3 and was compressed. The tampon product was tested for vaginal drying. This embodiment of the product of this invention was intended to alter the absorbency characteristics of its absorbent core. The protocol and evaluation of the panelists was the same as that used in Example 1. The results are shown in Table 5, below.

TABLE 5

| Score | Product A Control | Product E 50/50 Rayon/ Polyester Low Density |
|---|---|---|
| 0 | 5 | 9 |
| 1 | 6 | 2 |
| 2 | 2 | 1 |
| 3 | 2 | 0 |
| 4 | 0 | 0 |
| Totals | 15 | 12 |
| Avg. Score | 1.07 | 0.3 |

The Control Product A was the same as that of Example 1. These data illustrate that reducing vaginal drying can be achieved by substantially reducing the capillary suction pressure of the absorbent core.

EXAMPLE 5
In vitro Capillary Suction Pressure Test and Correlation with in vivo Results This test measures the reduction in pressure in a column of liquid behind a porous plate when the absorbent product is brought into contact with the porous plate. This test is more particularly described in copending U.S. patent application No. 996,476, filed Dec. 31, 1992, entitled "Method and Apparatus for Measuring the Capillary Attraction Developed by a Surface of an Absorbent Structure" (Yvon Levesque), which is hereby incorporated herein by reference. Generally, the capillarimeter provides a means for measuring the intensity of the capillary attraction developed at a surface of an absorbent body. The capillarimeter, which is depicted in FIG. 1, has the following elements: (1) a substantially closed cell capable of holding a certain quantity of liquid. The cell has an outer probing surface for contacting the absorbent body. The probing surface is in liquid-communication with an interior of said cell through an array of capillary passageways. (2) a pressure sensor mounted to said cell for observing a pressure of liquid therein, whereby contact between said probing surface and the absorbent body gives rise to capillary attraction acting on liquid in said capillary passageways, causing a pressure variation in said cell which is observed by said pressure sensor. The substantially closed cell has the capability of restraining the liquid from freely regressing from the capillary passageways under the influence of surface tension exerted by the absorbent body, thereby allowing to measure the intensity of the capillary attraction on the surface of the absorbent body without effecting any significant liquid transfer to the absorbent body.

The measuring device comprises a supporting plate 12 to which is mounted a vertically extending generally cylindrical receptacle 14 made of transparent hard plastic material. A pressure sensor 16 is mounted to the receptacle 14 to observe the magnitude of the pressure therein. The pressure sensor 16 is an electronic transducer generating an electric output signal proportional to the magnitude of the pressure in the receptacle 14.

On the top wall of the receptacle 14 is mounted a manually operated out-gassing valve 18 permitting to release air or other gases trapped in the receptacle 14.

A reservoir 19 is in fluid communication through a conduit 21 and through a manually operated valve 24 with the receptacle 14, for supplying test liquid thereto and to any other liquid containing chamber connected to the receptacle 14. During the normal use of the measuring device 10, the valve 24 is maintained closed to isolate the reservoir 19 from the receptacle 14. The valve 24 is opened only during the calibration and the preparation of the measuring device 10 for a test run, when desired for example to replenish the receptacle 14 with test liquid.

A small completely closed chamber 20 made of PLEXI-GLASS™ material is connected to the receptacle 14 through a flexible conduit 22 permitting to vertically displace the chamber 20 relative to the receptacle 14. A pressure head, either positive or negative, of the desired magnitude, can be established in the receptacle 14 to compensate any over pressure or under pressure therein. A mechanical lifting device is used to precisely locate the chamber 20 at the desired elevation relative to the receptacle 14. The capillarimeter also has a probe assembly 26 including a PLEXI-GLASS plate 28 in which is drilled a vertically extending bore 40. In the bore is 40 press-fitted an inverted cup-shaped housing 32 which holds a circular plate 34 made of fritted glass. The cup-shaped housing 32 completely encloses the plate 34, except its lower surface, which is flush with the lower surface of the plate and constitutes the probing surface of the capillarimeter.

The probe assembly 26 is movably connected to the supporting plate 12 by means of an arm 42.

The cup-shaped housing 32 is in fluid communication with the receptacle 14 through a flexible conduit 38. A manually operated out-gassing valve 40 is mounted on the top surface of cup-shaped housing 32 to evacuate air trapped therein.

The fritted glass plate 34 defines a three-dimensional array of capillary passageways establishing a multiplicity of fine fluid paths between the probing surface and the interior of the cup-shaped housing 32. When the capillary network is completely filled with liquid, air is prevented from entering therein even when the liquid is subjected to the influence of surface tension tending to suck liquid out from the exposed probing surface. Such surface tension occurs when the probing surface contacts a porous network whose capillary attraction is to be measured.

The pressure sensor 16, generating an electric output signal which represents the magnitude of pressure in the receptacle 14 can be used to drive an electronic display to provide a readout of the instantaneous pressure in the receptacle. Also, the pressure sensor 16 drives a chart plotter recording the evolution of pressure relative to time. The pressure recorded at 20 minutes is the pressure used to determine the surface capillary suction pressure reported herein.

Several commercial tampons and tampons produced according to Examples 2–4 were tested for their capillary suction pressure and in vivo drying scores. In addition, Product F is a tampon similar to Product E of Example 4. However, it was prepared using the cover material of Example 2, Product B. The test procedure followed those outlined above. The results of the in vivo and capillary suction pressure tests are included below in Table 6 along with density information for these tampons.

TABLE 6

| Tampon | in vivo Drying Score | Surface Capillary Suction Pressure (mm Hg) | Density (g/cm$^3$) |
| --- | --- | --- | --- |
| Product B | 0.73 | 80.7 | 0.37 |
| Product C | 0.67 | 57.6 | 0.43 |
| Product D | 0.5 | 35 | 0.43 |
| Product E | 0.37 | 35.8 | 0.19 |
| Product F | 0.32 | 24.2 | 0.22 |
| Tampax Compak ™ Regular | 1.07 | 137 | 0.56 |
| Playtex ™ Plastic Regular | 0.92 | 79.9 | 0.39 |
| o.b. ™ Regular | 1.0 | 82.3 | 0.40 |
| Playtex Ultimates ™ Regular | 1.33 | 91.7 | 0.29 |
| Kotex Security ™ Regular | 1.33 | 52 | 0.34 |

FIG. 2 is a graph showing the correlation between the capillary suction pressure exerted by the various tampons and their in vivo drying scores for the data included in Table 6. The relation between these parameters illustrate in Table 6 and FIG. 2 provides a correlation coefficient, r, equal to 0.65. Thus, tampon products having low capillary suction pressure will also exhibit low drying in vivo. The tampons of this invention are designed to hold the prescribed amount of body secretions, according to its Syngina absorbency rating as does a conventional tampon, without exerting a capillary suction pressure sufficient to cause drying of the vaginal epithelium.

The specification and examples above are presented to aid in the complete and non-limiting understanding of the invention disclosed herein. Since many variations and embodiments of the invention can be made without departing from its spirit and scope, the invention resides in the claims hereinafter appended.

We claim:

1. A method of preserving natural moisture of vaginal epithelial tissue during use of a tampon having an absorbent core and an outer surface, the method comprising the steps of inserting the tampon, the tampon having an initial capillary suction pressure at the outer surface thereof of less than about 40 mm Hg; allowing the tampon to absorb vaginal secretions without substantially drying the vaginal epithelial tissue; and removing the tampon.

2. The method of claim 1 wherein the tampon further comprises a semipermeable membrane of woven or non-woven fibers at the outer surface.

3. The method of claim 1 wherein the absorbent core comprises fibers having a denier of at least about 3.

4. The method of claim 1 wherein the absorbent core has a density which is equal to or less than about 0.25 g/cc.

5. The method of claim 1 wherein the absorbent core comprises a sufficient amount of hydrophobic materials to reduce capillary suction pressure at the outer surface.

6. The method of claim at wherein the absorbent core comprises about 10 to 90 wt-% of the hydrophobic materials.

7. The method of claim 6 wherein the absorbent core comprises about 30 to 70 wt-% of the hydrophobic materials.

8. The method of claim 7 wherein the absorbent core comprises about 50 wt-% of the hydrophobic materials.

* * * * *